United States Patent
Ji et al.

(10) Patent No.: US 9,480,474 B2
(45) Date of Patent: Nov. 1, 2016

(54) LINEAR CUTTING ELEMENT WITH E-SHAPED GUIDING ELEMENT

(75) Inventors: Rong Ji, Jiangsu (CN); Weimin Yang, Jiangsu (CN); Xingfang Liu, Jiangsu (CN); Yuhong Wang, Jiangsu (CN); Long Rui, Jiangsu (CN)

(73) Assignee: CHANGZHOU KANGDI MEDICAL STAPLER CO., LTD., Xinbei District, Changzhou, Jiangsu (CN)

( * ) Notice: Subject to any disclaimer, the term of this patent is extended or adjusted under 35 U.S.C. 154(b) by 218 days.

(21) Appl. No.: 14/387,837

(22) PCT Filed: Aug. 31, 2012

(86) PCT No.: PCT/CN2012/080842
§ 371 (c)(1),
(2), (4) Date: Sep. 24, 2014

(87) PCT Pub. No.: WO2013/143257
PCT Pub. Date: Oct. 3, 2013

(65) Prior Publication Data
US 2015/0119904 A1 Apr. 30, 2015

(30) Foreign Application Priority Data
Mar. 31, 2012 (CN) .......................... 2012 1 0091043

(51) Int. Cl.
*A61B 17/04* (2006.01)
*A61B 17/072* (2006.01)
*A61B 17/06* (2006.01)
*A61B 17/32* (2006.01)
*A61B 17/00* (2006.01)

(52) U.S. Cl.
CPC ..... *A61B 17/0469* (2013.01); *A61B 17/06166* (2013.01); *A61B 17/072* (2013.01); *A61B17/320016* (2013.01); *A61B 2017/00818* (2013.01); *A61B 2017/07271* (2013.01); *A61B 2017/07285* (2013.01); *A61B 2017/320052* (2013.01)

(58) Field of Classification Search
CPC .................. A61B 17/0469; A61B 17/320016; A61B 17/06166; A61B 2017/00818
USPC .......................... 606/144, 139, 153, 219, 151
See application file for complete search history.

(56) References Cited

U.S. PATENT DOCUMENTS

| | | | | |
|---|---|---|---|---|
| 7,204,404 B2 * | 4/2007 | Nguyen | ............... | A61B 17/072 227/175.1 |
| 7,717,312 B2 * | 5/2010 | Beetel | .................. | A61B 17/068 227/175.1 |
| 8,267,302 B2 * | 9/2012 | Farascioni | ....... | A61B 17/07207 227/179.1 |
| 9,113,869 B2 * | 8/2015 | Racenet | ............... | A61B 17/072 |

* cited by examiner

*Primary Examiner* — Vy Bui
(74) *Attorney, Agent, or Firm* — Global IP Service; Tianhua Gu

(57) ABSTRACT

A linear cutting element (1) with an E-shaped guiding element (16) enables the suture and cutting of surgery to be simultaneously conducted when being loaded in a linear cutting anastomat (2). The linear cutting element (1) comprises a knife underlaying plate (10), a nail abutting seat (11), an assembly cover (12), suture nails (13), a nail cartridge (14), a push sheet (15), a guiding element (16), a pin (17) for the guiding element, a cutting knife (18), a knife stand (19), a positioning needle (20), a positioning needle holder (21) and a blank cap (22). The knife underlaying plate (10) and the nail abutting seat (11) are fixedly connected through a front-end groove (101) and rear-end agnails (102, 103) of the knife underlaying plate (10). The nail abutting seat (11) is fixedly connected to the guiding element (16) through the pin (17) for the guiding element. The guiding element (16) is placed at the open end of the nail cartridge (14), and the guiding element (16) enables nail grooves (122) at the two sides of the nail cartridge (14) to remain parallel vertically, which enables the nail cartridge (14) in an open state to be in a closed state. The assembly cover (12) is arranged between the nail abutting seat (11) and the nail cartridge (14), and can be removed from the linear cutting element (1). The linear cutting element (1) is replaceably loaded into the linear cutting anastomat (2).

9 Claims, 15 Drawing Sheets

LINEAR CUTTING ELEMENT WITH E-SHAPED GUIDING ELEMENT

CROSS REFERENCE TO RELATED PATENT APPLICATION

The present application is the US national stage of PCT/CN2012/080842 filed on Aug. 31, 2012, which claims the priority of the Chinese patent applications No. 201210091043.6 filed on Mar. 31, 2012, which applications are incorporated herein by reference.

BACKGROUND OF THE PRESENT INVENTION

Field of Invention

The invention relates to the field of surgical medical instruments, in particular to a linear cutting element with an E-shaped guiding element, which enables the suture and cutting of surgery to be simultaneously conducted when being loaded in a linear cutting anastomat.

Description of Related Arts

The linear anastomat, also known as a digestive tract closure, is an instrument to linearly drive a plurality of mutually staggered suturing nails in the tissue, and is one of the instruments widely used to replace the manual linear suture. It mainly used to suture closure stomach, duodenum, small intestine, colon stump for a whole layer exstrophy suture.

In the case of difficulty in revealing operative field, surgeons are often faced with many challenges, such as: 1) the instrument is hard to enter the lower position of the pelvis; 2) the instrument would block the operative field; 3) sometimes a variety of instruments are needed to adapt different pelvic cavity structure; 4) in the lower pelvis, there is no room for the operations of cutting and suture; 5) how to reduce the tissue trauma and chances of infection, etc.

Currently, the traditional linear anastomat exists one drawback, i.e., it only has suturing function, but without cutting function, which is inconvenience for operation. In order to isolate the excess tissue, a blade is needed to accomplish an artificial excision. However, since the surgeons have varied operating skills and cutting practices, the tissue would be damaged as a sharp separation is conducted or the tool is isolated from the electric.

SUMMARY OF THE PRESENT INVENTION

The object of the present invention is to overcome the disadvantages of the prior art, and to provide a linear cutting element with an E-shaped guiding element, which is a linear cutting element enabling the suture and cutting of surgery to be simultaneously conducted at surgery. The linear cutting element is loaded in a linear cutting anastomat, and pushes a bottom of a tool apron by a driving board of the anastomat, then an end face of the tool apron pushes a bottom of a push sheet, suturing nails on an end face of the push sheet conduct a movement of tissue suture in relative to a molding groove of a nail abutting plate, and a cutting tool fixed on a tool apron conduct a movement of tissue cutting, so that the suture and cutting of the tissue are simultaneously achieved in one operation.

The linear cutting element with an E-shaped guiding element of the present invention is accomplished by the following technical solution: The linear cutting element with an E-shaped guiding element comprises a tool underlying plate, a nail abutting seat, an assembly cover, a suturing nail, a nail cartridge, a push sheet, a guiding element, a guiding element pin, a cutting tool, a tool apron, a positioning needle, a positioning needle holder and a blank cap; the tool underlying plate and the nail abutting seat are fixedly connected by a front-end groove and a rear-end barb of the tool underlying plate.

The nail abutting seat is fixedly connected with the guiding element by the guiding element pin.

The guiding element is arranged at an open end of the nail cartridge, and the guiding element enables nail grooves at the two sides of the nail cartridge to remain parallel vertically, which enables the nail cartridge in an open state to be in a closed state.

The assembly cover is arranged between the nail abutting seat and the nail cartridge, and can be removed from the linear cutting element.

The linear cutting element can be replaceably loaded into the linear cutting anastomat.

The guiding element is in clearance fit with the nail cartridge, and both the guiding element and the nail cartridge can move vertically relative to each other.

The cross profile of the guiding element is an E-shape.

One end of the nail cartridge is open.

The middle of the nail cartridge is provided with at least one positioning boss for a cutting tool.

The tool apron is provided with at least two slots to receive the driving board of the linear cutting anastomat.

The nail abutting seat shows an L-shape.

One end of the assembly cover is an elastic finger.

The linear cutting element with an E-shaped guiding element of the present invention features reasonable design, and compact structure. After the linear cutting element is loaded in a linear cutting anastomat, pushes the bottom of the tool apron by a driving board of the anastomat, then the endface of the tool apron pushes the bottom of the push sheet, suturing nails on a end of the push sheet conduct a movement of tissue suture in relative to a molding groove of a nail abutting plate, and a cutting tool fixed on a tool apron conduct a movement of tissue cutting, so that the suture and cutting of the tissue are simultaneously achieved in one operation.

By applying the above technical solution, it avoids the cumbersome operation of firstly operating suture by a traditional abastomat, followed by manual excision by a scalpel, as well as the complication caused by the respectively operations of suture and cutting at surgery. It simultaneously sutures and cuts the tissue in one operation, namely, accomplishes the movements of suture and cutting; the linear cutting element is used, on one hand, to reduce the amount of tools for surgery, and on the other hand, to simplify the operation procedure of surgery, thereby utmost reducing the contamination at surgery, and increasing the visuality of the operative field. The invention features simple and useful clinic operation, and is more popular than the traditional instrument.

BRIEF DESCRIPTION OF THE DRAWINGS

Hereinafter, detailed description of the present invention is illustrated in combination with the drawings.

DETAILED DESCRIPTION OF THE PREFERRED EMBODIMENTS

Hereinafter, detailed description of the present invention is illustrated in combination with the drawings and embodiments.

Figure 1:
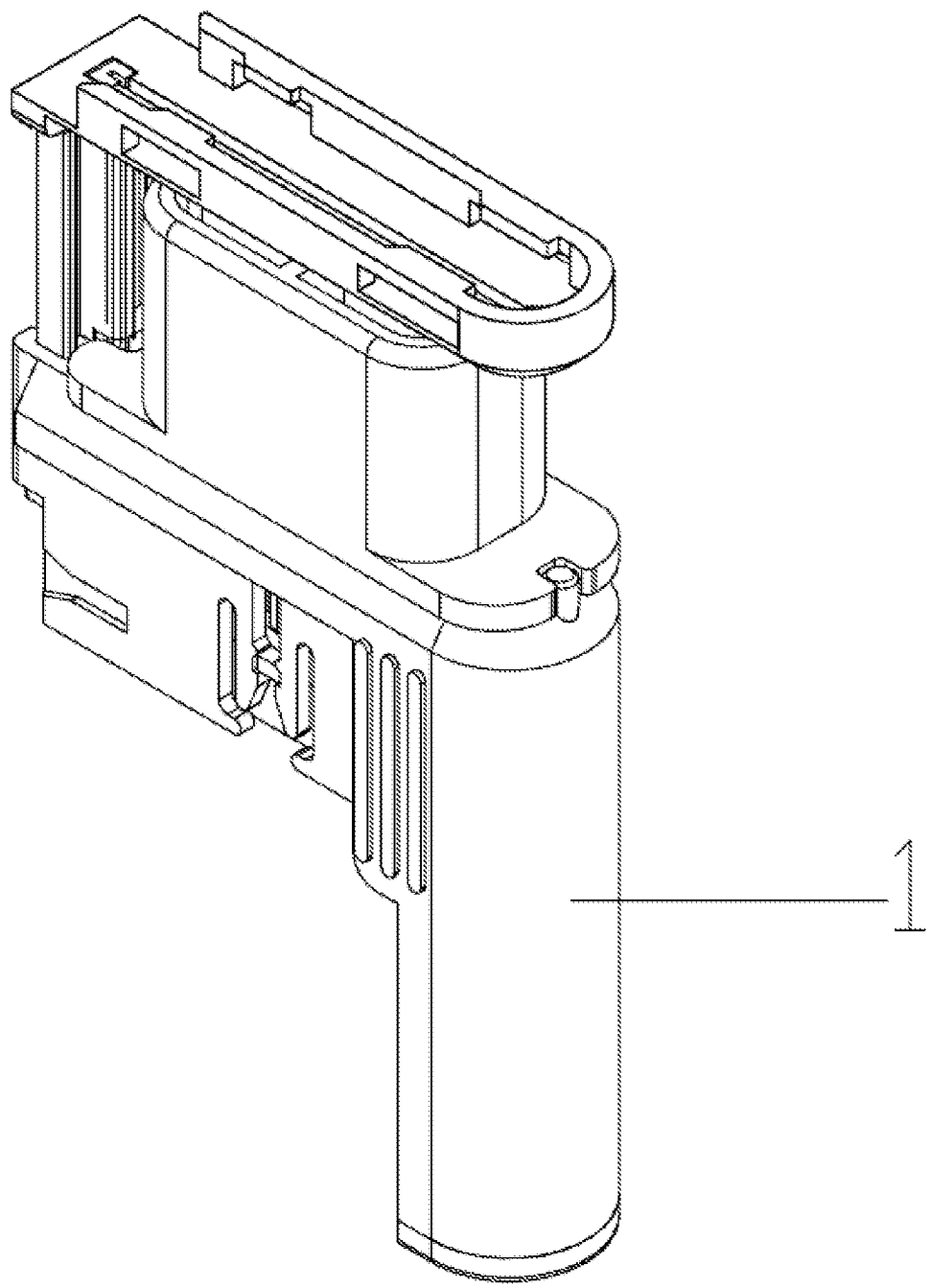
FIG. 1 is a structure schematic diagram of a cutting element of the present invention.
Figure 2:
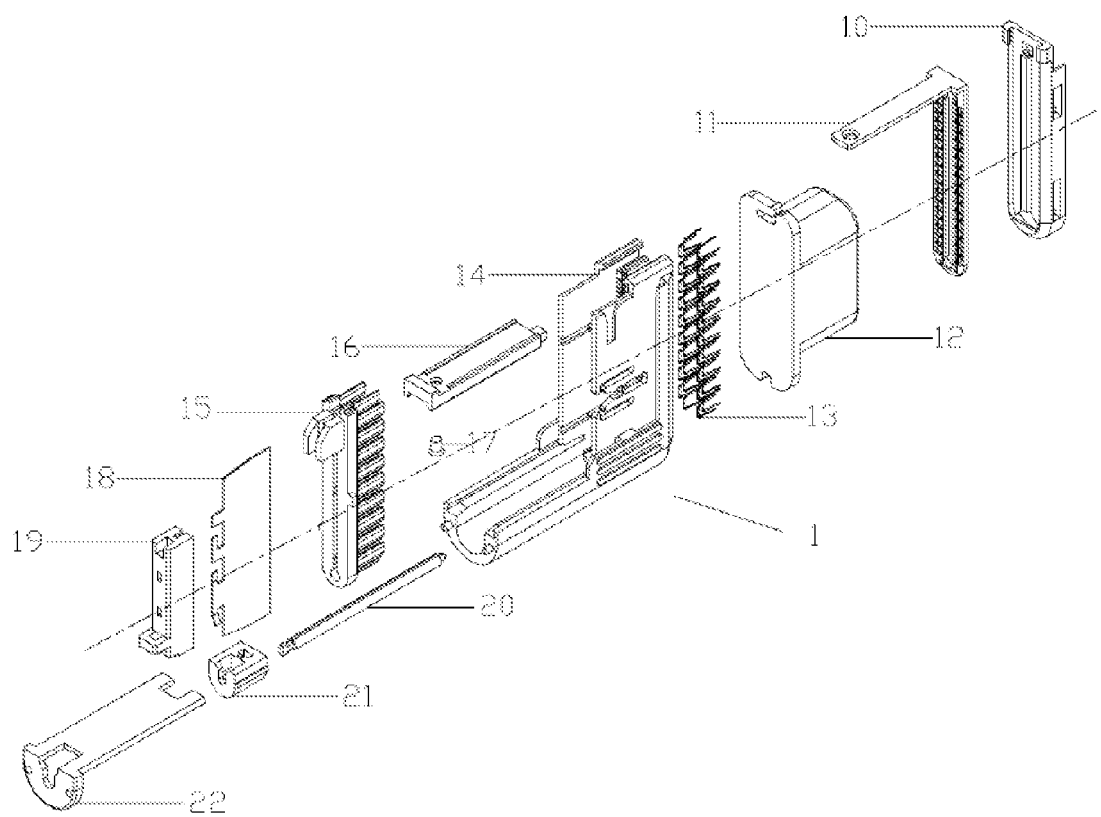
FIG. 2 is a structure exploded diagram of the cutting element of the present invention.

As shown in FIGS. 1 and 2, the linear cutting element with an E-shaped guiding element comprises a tool underlying plate 10, a nail abutting seat 11, an assembly cover 12, suturing nails 13, a nail cartridge 14, a push sheet 15, a guiding element 16, a guiding element pin 17, a cutting tool 18, a tool apron 19, a positioning needle 20, a positioning needle holder 21 and a blank cap 22; The linear cutting element can be loaded into the linear cutting anastomat in a replaceable mode.

The tool underlying plate 10 and the nail abutting seat 11 are fixedly connected by a front-end groove and a rear-end barb of the tool underlying plate 10.

The nail abutting seat 11 is fixedly connected with the guiding element 16 by the guiding element pin 17.

The guiding element 16 is arranged at an open end of the nail cartridge 14, and the guiding element 16 enables nail grooves at the two sides of the nail cartridge 14 to remain parallel vertically, which enables the nail cartridge 14 in an open state to be in a closed state. The assembly cover 12 is arranged between the nail abutting seat 11 and the nail cartridge 14, and the assembly cover 12 can be removed from the linear cutting element.

The guiding element 16 is in clearance fit with the nail cartridge 14, and both the guiding element 16 and the nail cartridge 14 can move vertically relative to each other.

The cross profile of the guiding element 16 is an E-shape. One end of the nail cartridge 14 is open.

The middle of the nail cartridge 14 is provided with at least one positioning boss for the cutting tool.

The tool apron 19 is provided with at least two slots for housing the driving board of the linear cutting anastomat.

The nail abutting seat 11 shows an L-shape.

One end of the assembly cover 12 is an elastic finger.

Figure 3:
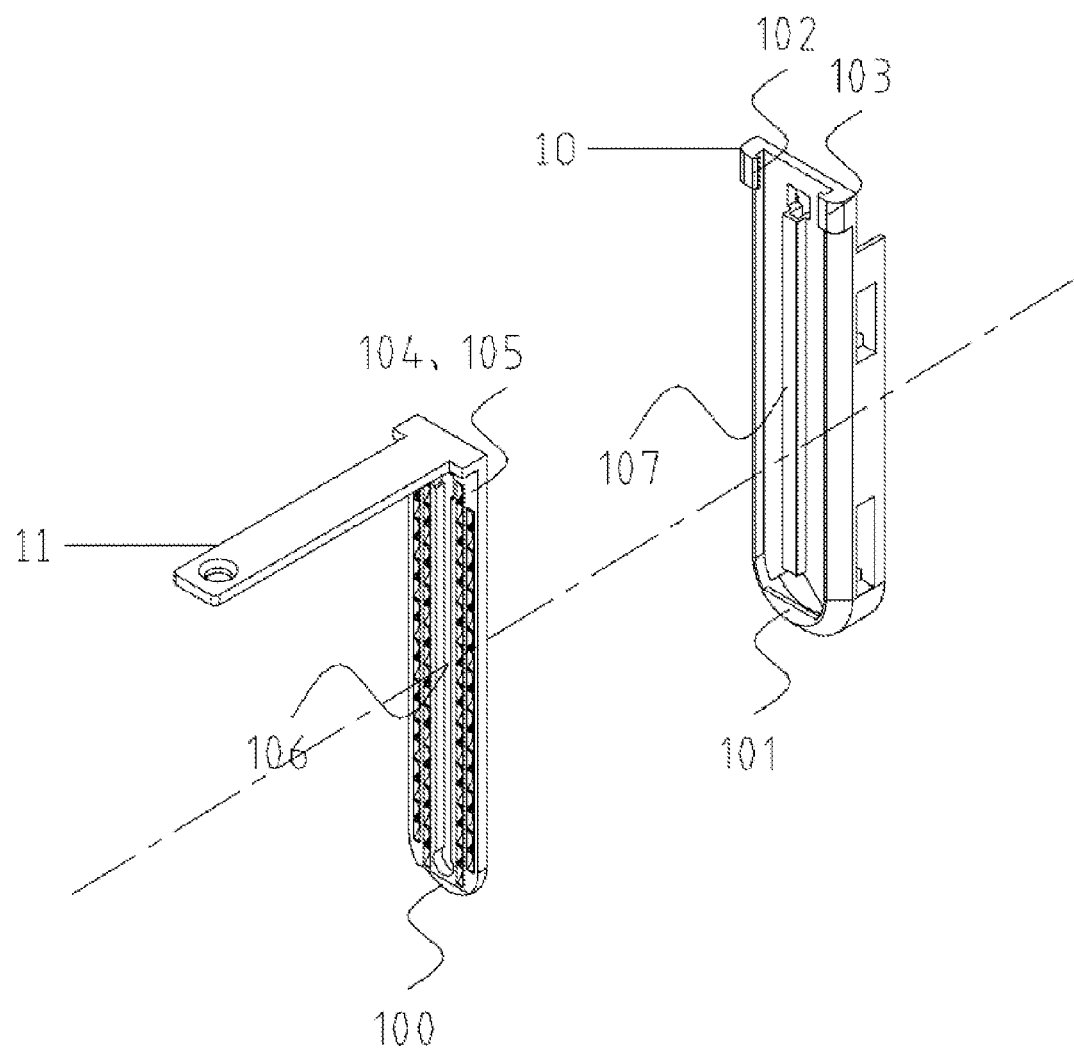
FIG. 3 is a structure schematic diagram of a tool underlying plate and a nail abutting plate of the present invention.
Figure 4:
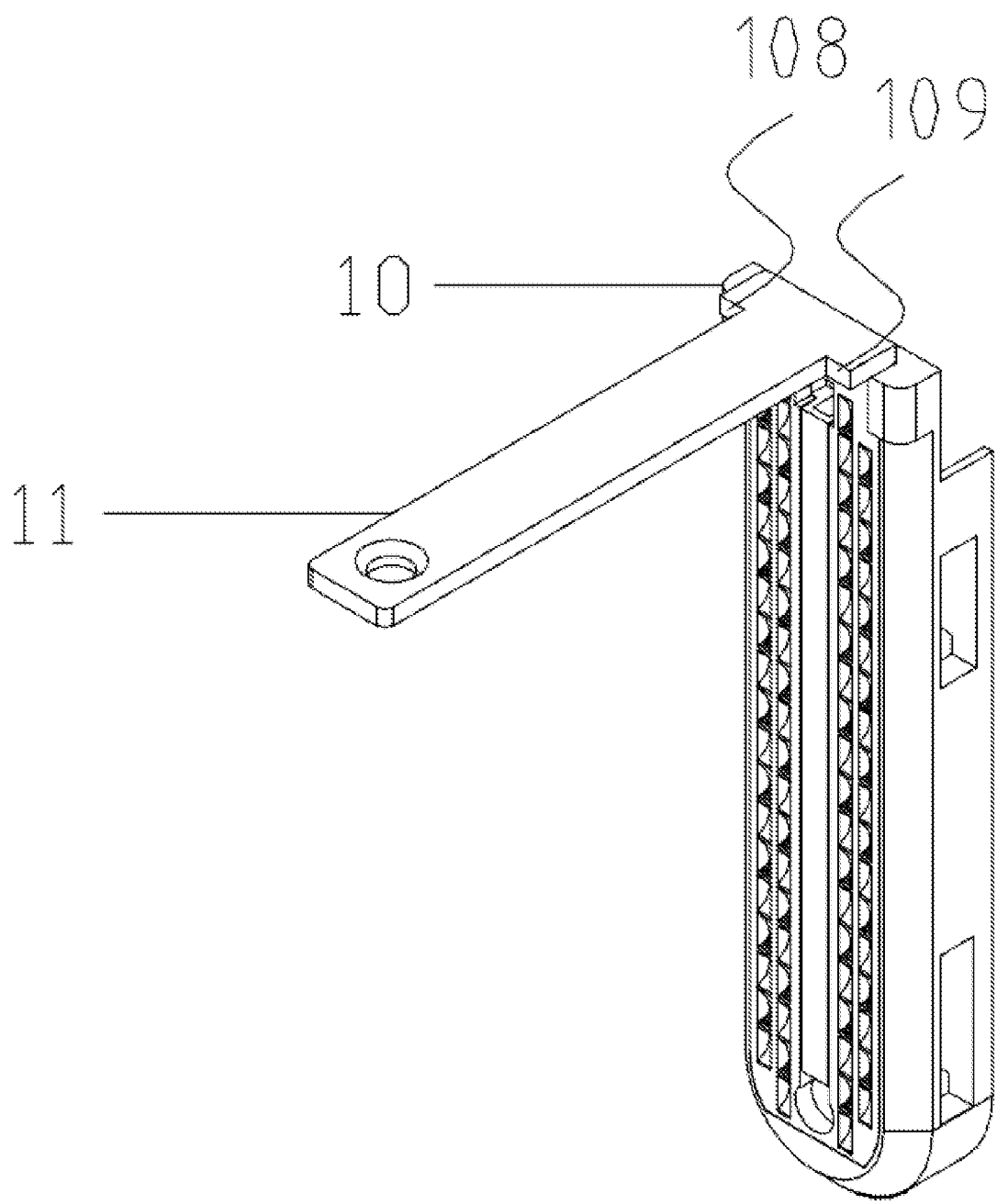
FIG. 4 is an assembly schematic diagram of the tool underlying plate and the nail abutting plate of the present invention.

As shown in FIGS. 3 and 4, the nail abutting seat 11 is fixed with the tool underlying plate 10, the front-end tab 100 of the nail abutting seat 11 is arranged at the front-end groove 101 of the tool underlying plate 10, the rear-end planes 104, 105 of the nail abutting seat 11 is arranged at the rear-end barbs 102, 103 of the tool underlying plate 10, a elongated slot 106 at the middle of the nail abutting seat 11 is arranged at a boss 107 at the middle of the tool underlying plate 10.

Figure 5:
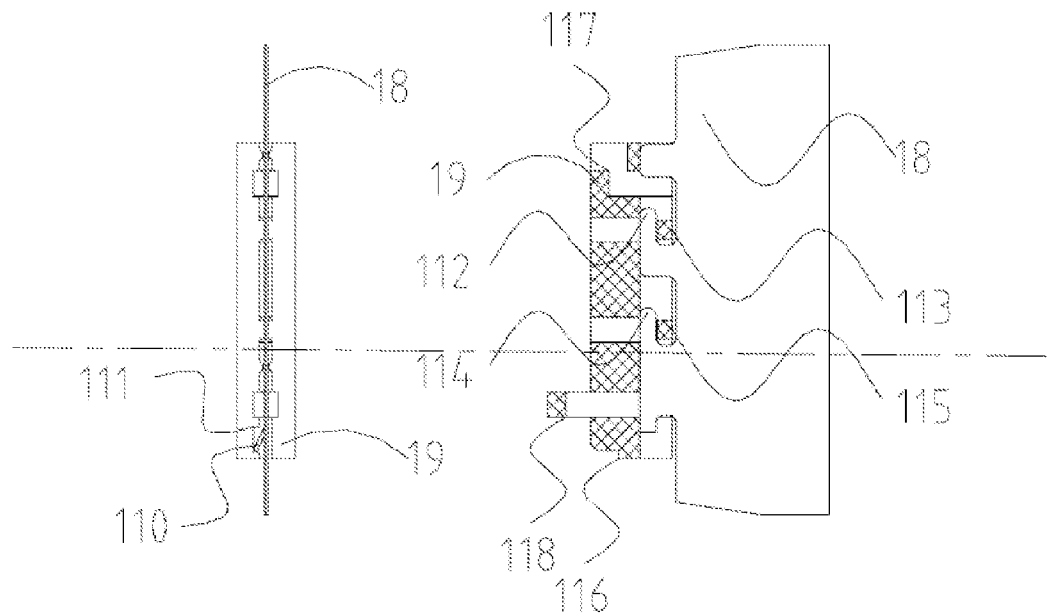
FIG. 5 is a structure planar diagram of a tool apron and a cutting tool of the present invention.
Figure 6:
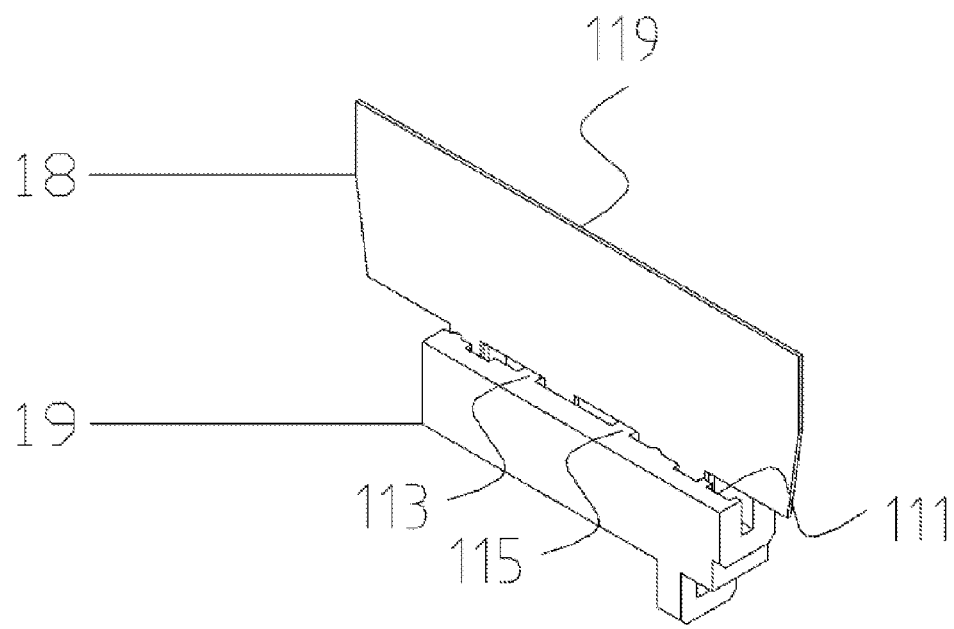
FIG. 6 is a structure stereogram of the tool apron and the cutting tool of the present invention.

As shown in FIGS. 5 and 6, the cutting tool 18 is fixed with the tool apron 19, the tabs 110, 112, 114 of the cutting tool 18 is arranged at the grooves 111, 113, 115 of the tool apron 19. Slots 117, 118 of the tool apron 19 are used to receive the driving board of the linear cutting anastomat.

Figure 7:
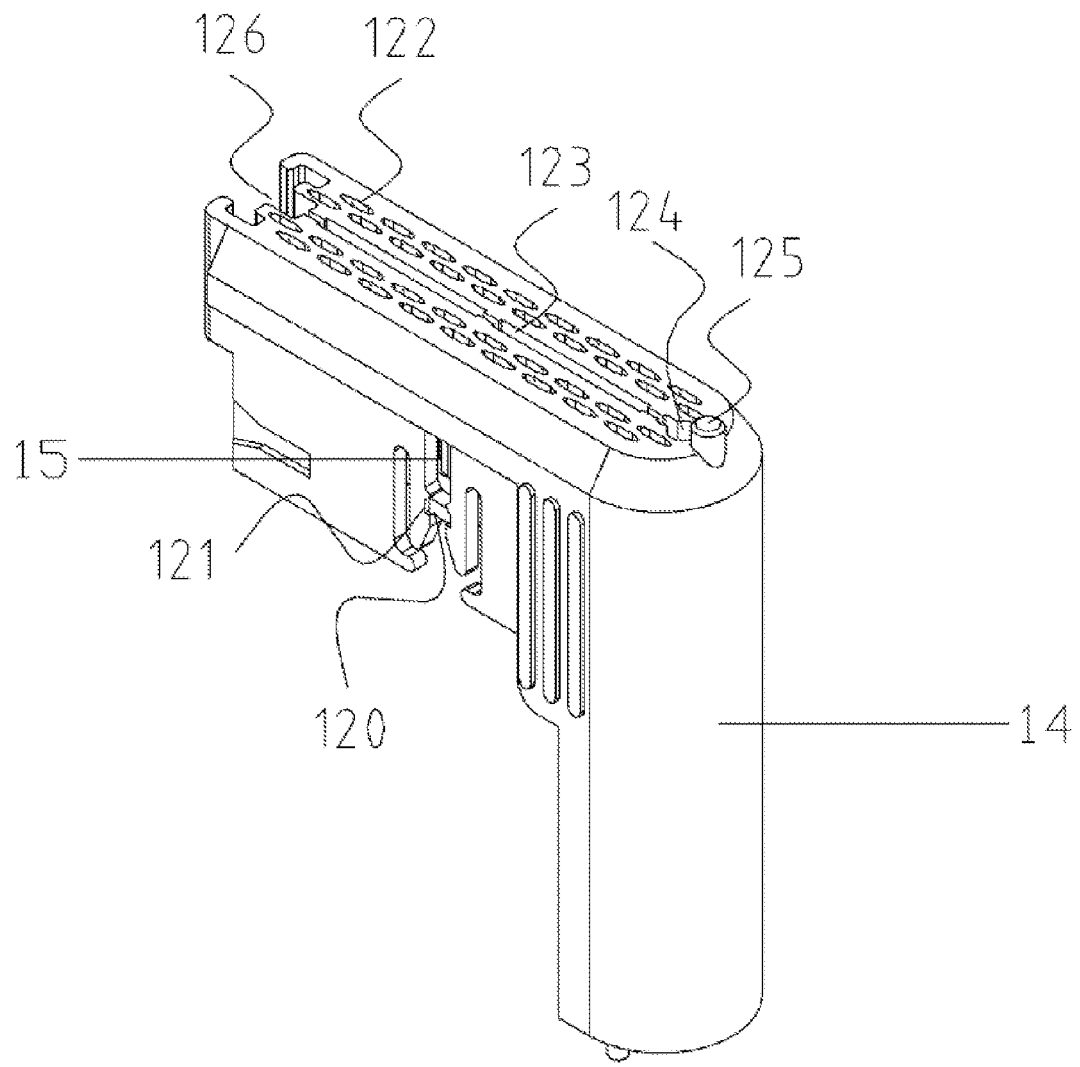
FIG. 7 is a structure schematic diagram of a nail cartridge and a push sheet of the present invention.

As shown in FIG. 7, the push sheet 15 is arranged at the nail slot 122 of the nail cartridge 14, the boss 120 of the push sheet 15 is arranged at the elastic latch 121 of the nail cartridge 14, one end 126 of the nail cartridge 14 is open, and the nail cartridge 14 contains a feed slot 123, a location hole 123 and a limit boss 125.

Figure 8:
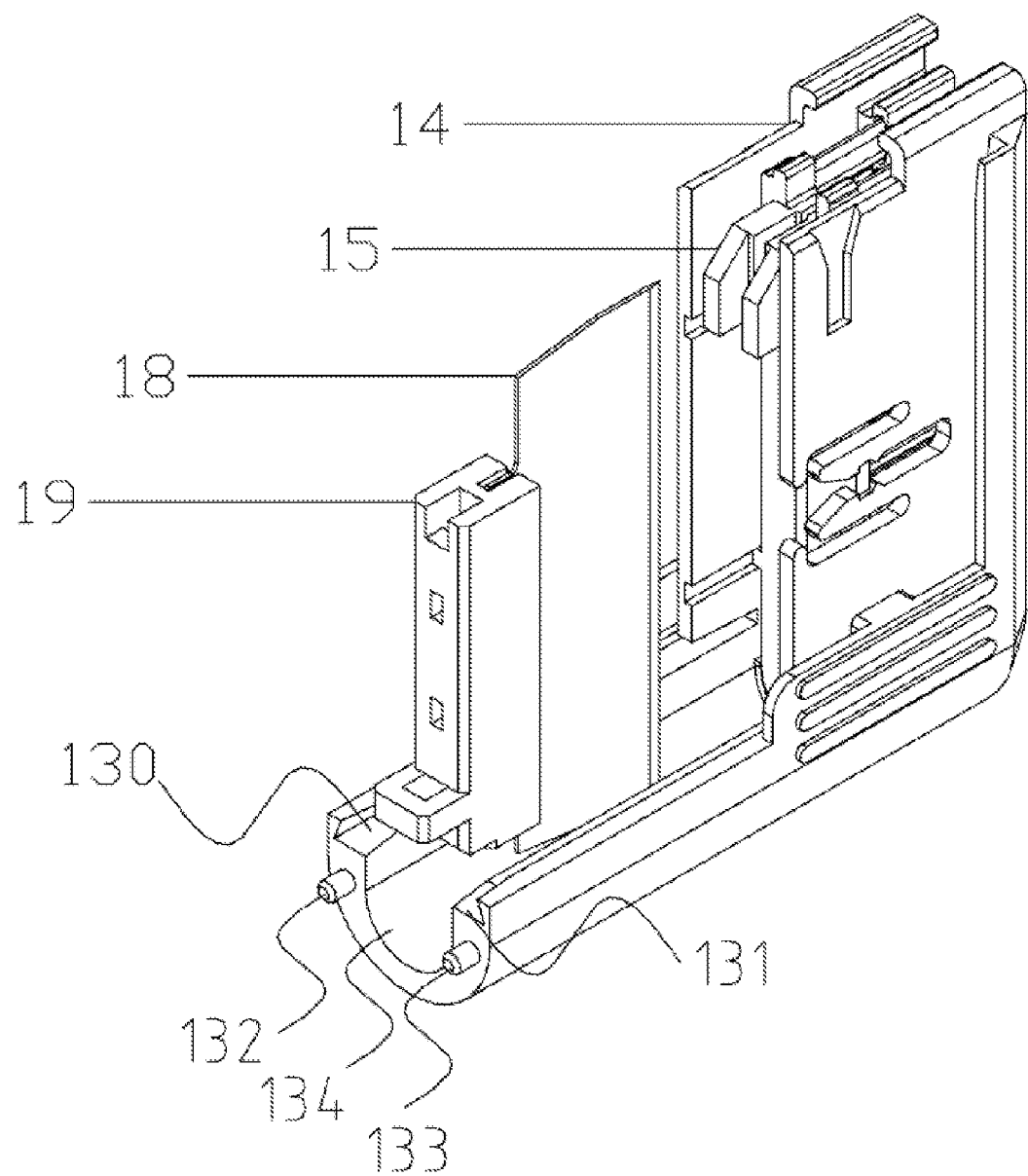
FIG. 8 is a structure schematic diagram of parts in FIGS. 6 and 7 of the present invention.
Figure 9:
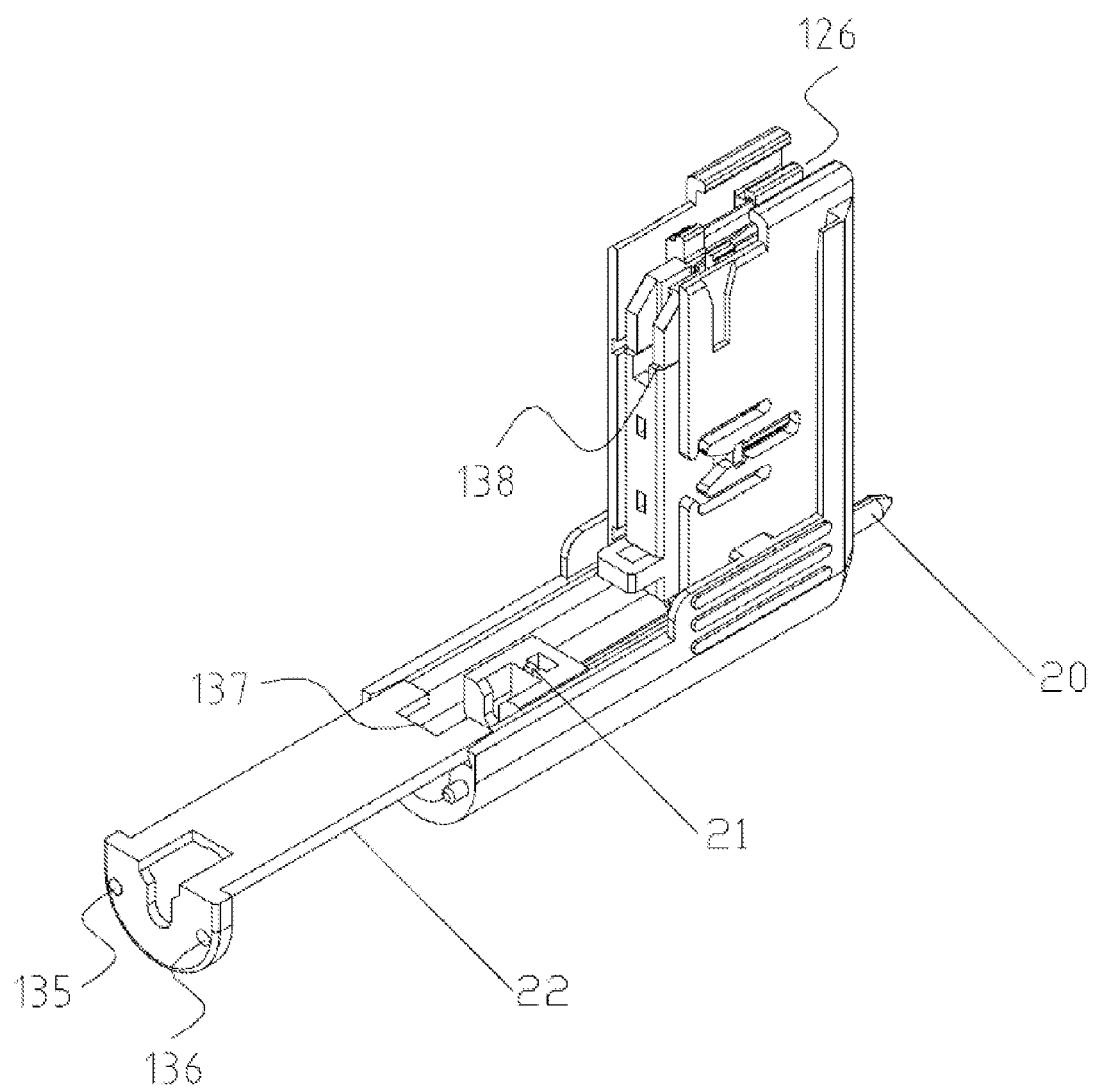
FIG. 9 is a structure schematic diagram of parts in FIG. 8 and other parts of the present invention.

As shown in FIGS. 8 and 9, the cutting tool 18 and the tool apron 19 are arranged at the rear-end of the push sheet 15, the front-end 119 of the cutting tool 18 traverses the feed slot 123 located between the nail cartridge 14 and the push sheet 15, the positioning needle 20 is fixedly connected with the positioning needle holder 21 through a connecting neck 150, the positioning needle 20 traverses the location hole 124 of the nail cartridge 14, the blank cap 22 slides into the slots 130, 131 of the nail cartridge 14, holes 135, 136 of the blank cap 22 are positioned in the bosses 132, 133 of the nail cartridge 14. The positioning needle holder 21 can move in a cavity 134 of the nail cartridge 14. One end of the tool apron 19 is supported by the groove face 137 of the blank cap 22, and the other end is supported by a side face 138 of the push sheet 15.

Figure 10:
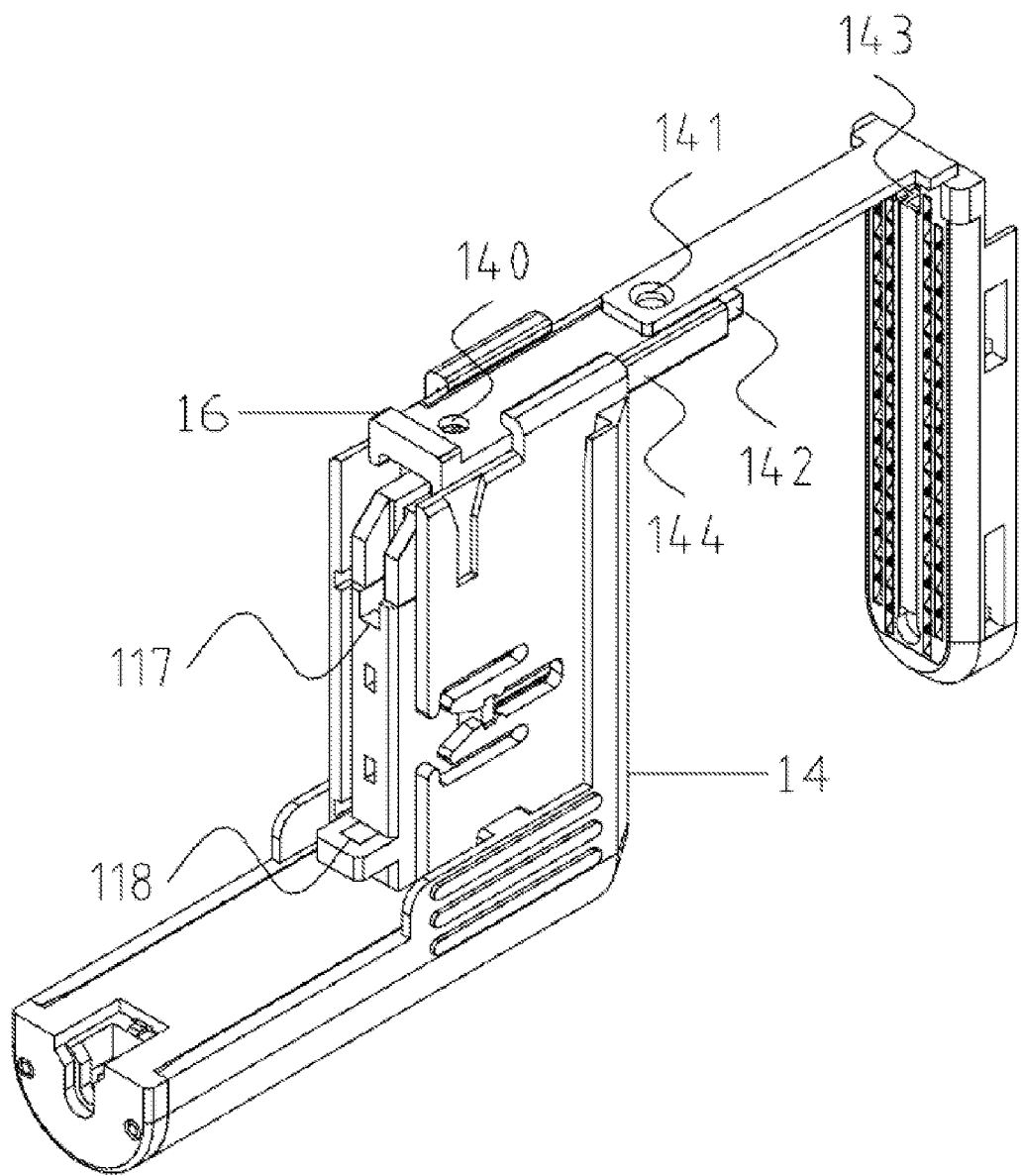
FIG. 10 is a structure schematic diagram of parts in FIGS. 4 and 9, and a guiding element of the present invention.
Figure 11:
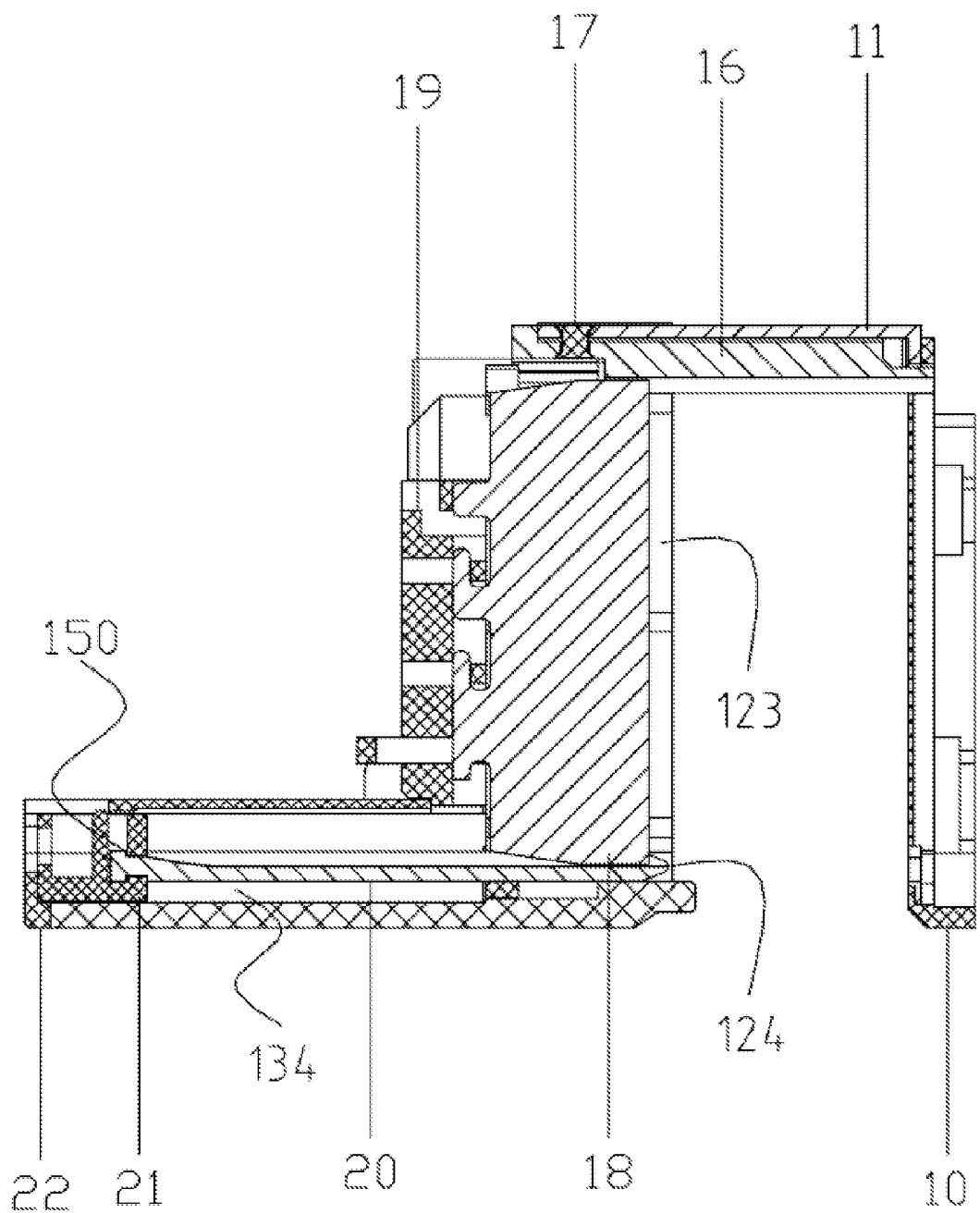
FIG. 11 is a structure section view of the cutting element in an initial status of the present invention.

As shown in FIGS. 10 and 11, the guiding element 16 with an E-shaped face 144 is arranged at the open end 126 of the nail cartridge 14, and its boss 142 is arranged at the groove 143 of the nail abutting plate 11, and its location hole 140 is fixedly connected with a hole 141 of the nail abutting plate 11 through the guiding element pin 17.

Figure 12:
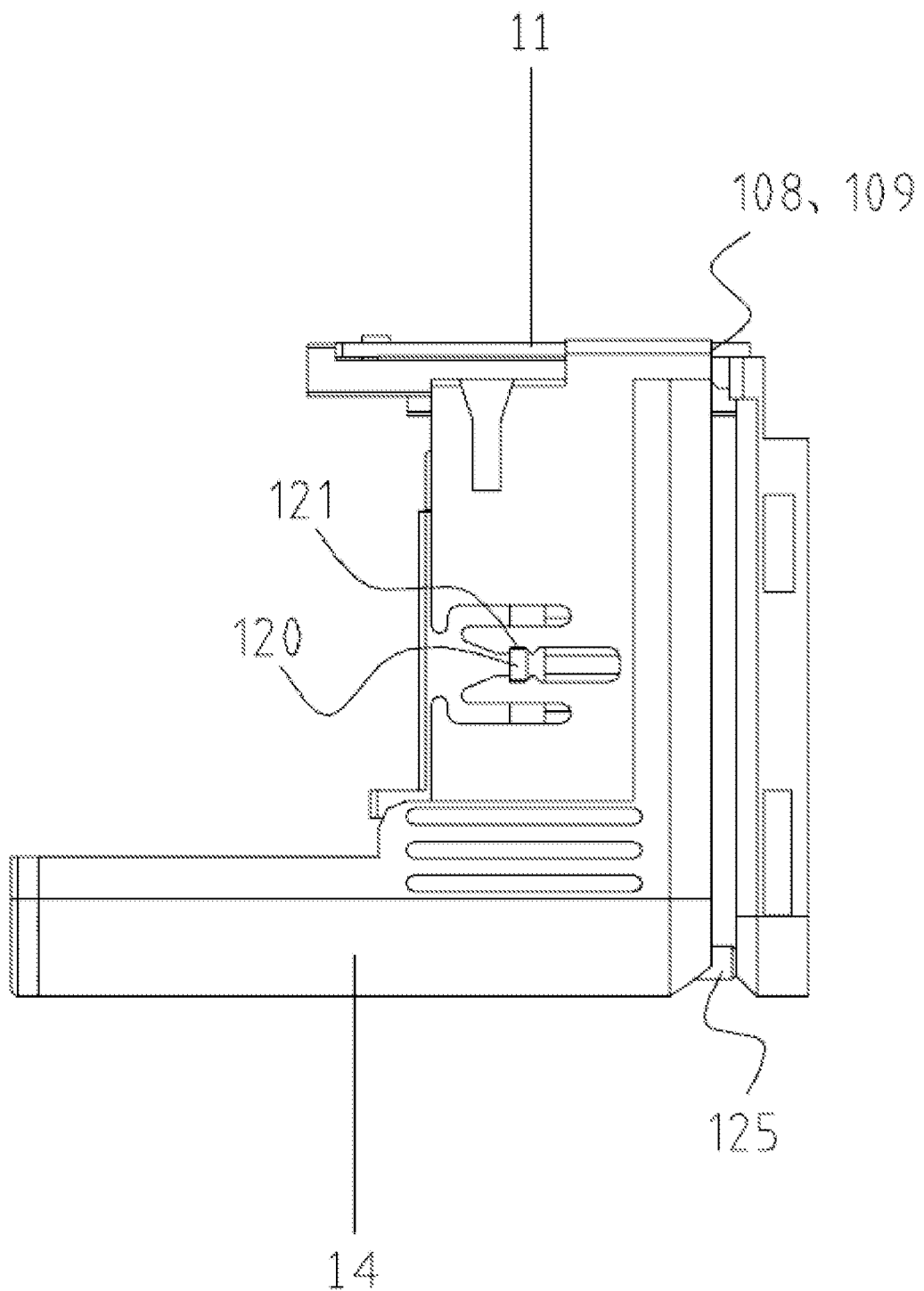
FIG. 12 is a structure schematic diagram of the cutting element in a closed status of the present invention.

As shown in FIG. 12, the nail abutting plate 11 and the nail cartridge 14 are oppositely installed, to control the closed gap of the linear cutting element through limit steps 108, 109 of the nail abutting plate 11 and the limit boss 125 of the nail cartridge 14.

Figure 13:
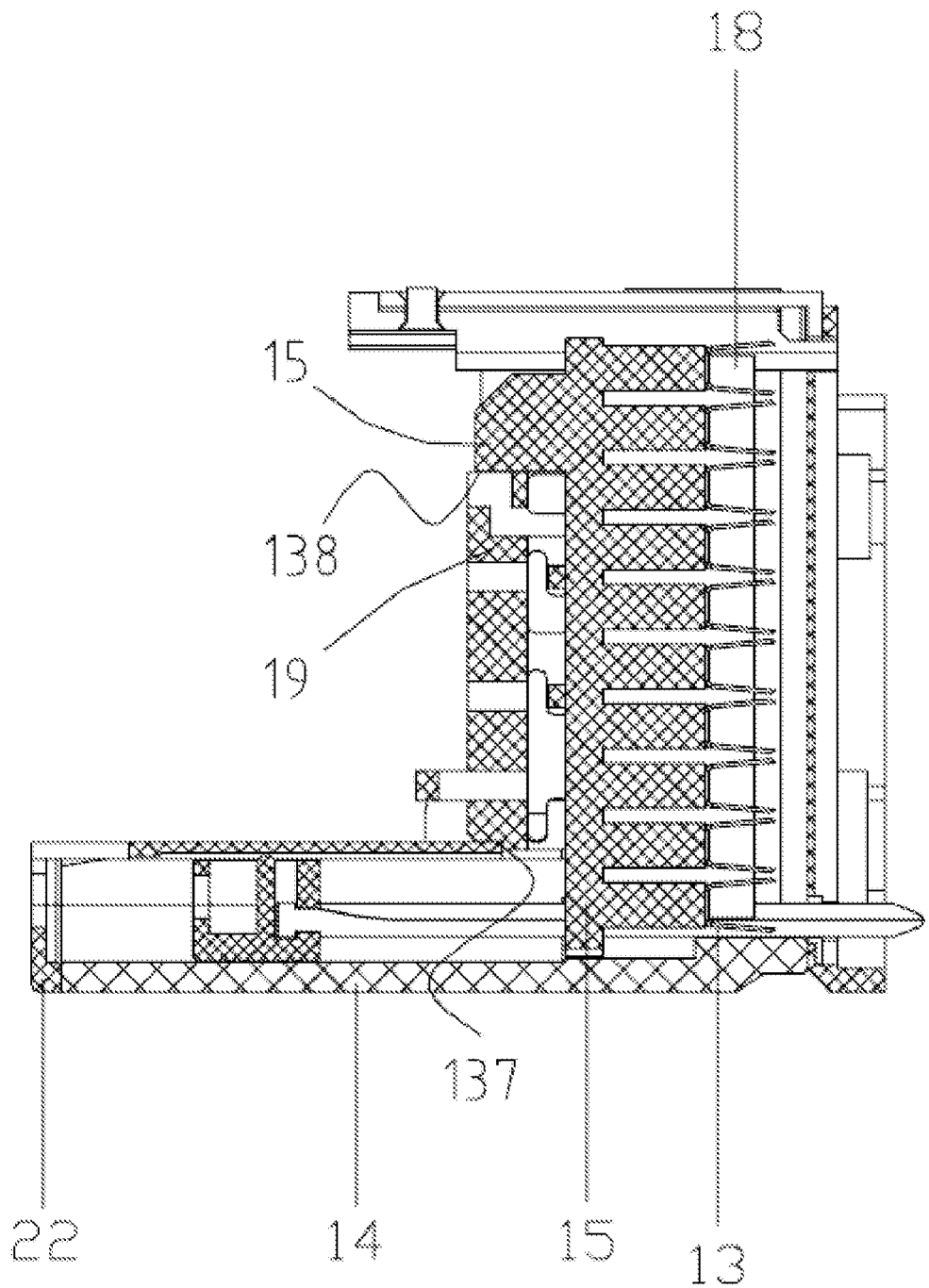
FIG. 13 is a structure section view of the cutting element in a closed status of the present invention.

As shown in FIG. 13, the nail cartridge 14 is equipped with the push sheet 15, the end of the push sheet 15 is equipped with the suturing nails 13.

Figure 14:
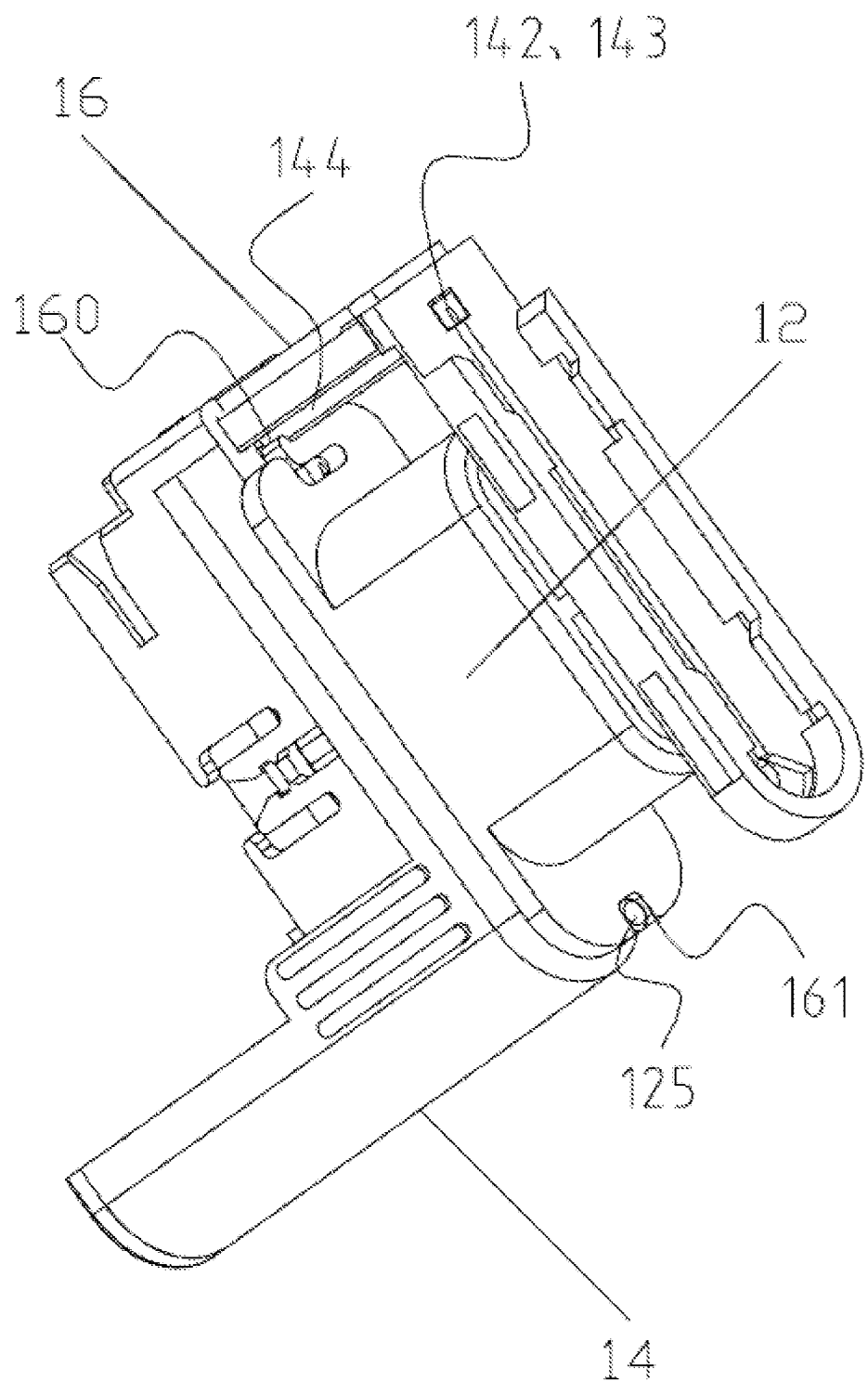
FIG. 14 is a structure schematic diagram of parts in FIG. 10, and an assembly cover of the present invention.

As shown in FIG. 14, the assembly cover 12 is arranged between the nail abutting plate 11 and the nail cartridge 14. An opening 161 at one end of the assembly cover 12 is arranged at the boss 125 of the nail cartridge 14, and a elastic finger 160 at the other end of the assembly cover 12 is arranged at one side of the E-shaped face 144 of the guiding element 16.

Figure 15:
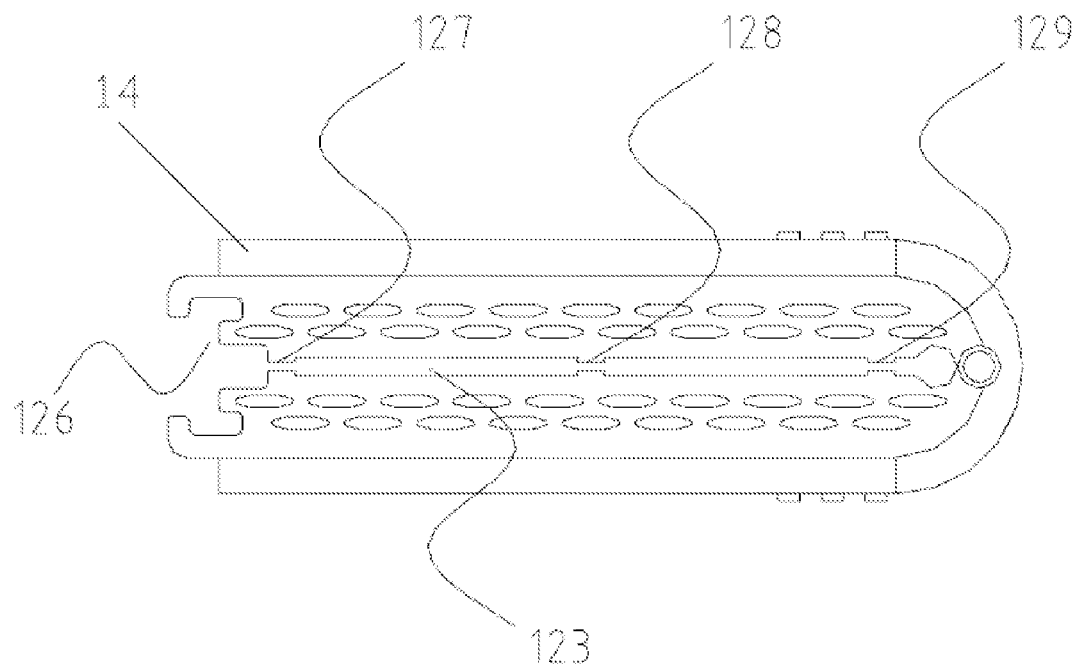
FIG. 15 is a structure schematic diagram of a positioning boss for cutting tool at the middle of the nail cartridge of the present invention.
Figure 16:
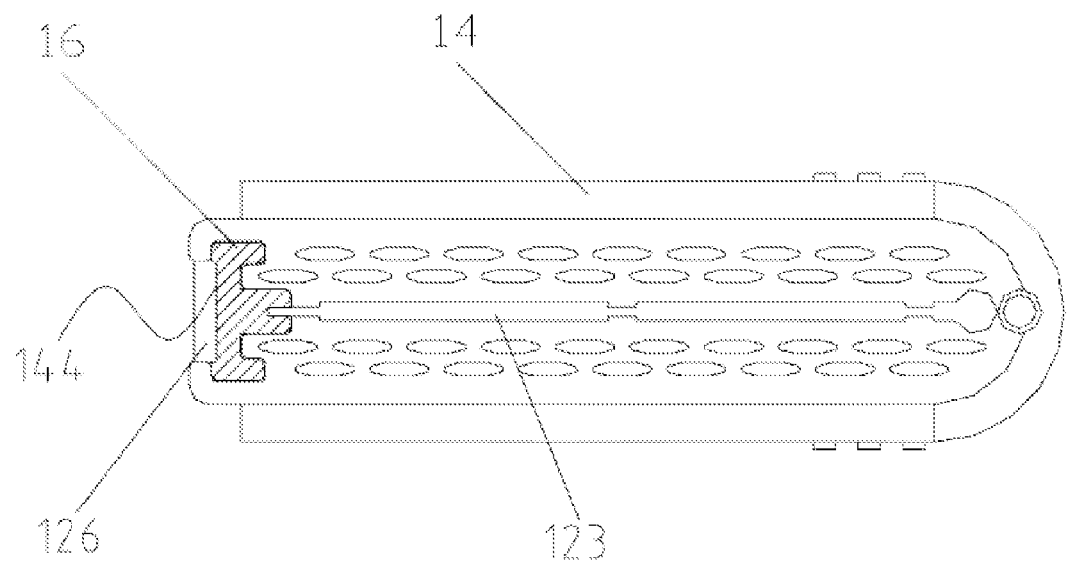
FIG. 16 is a structure schematic diagram of an E-shaped guiding element of the present invention.
Figure 17:
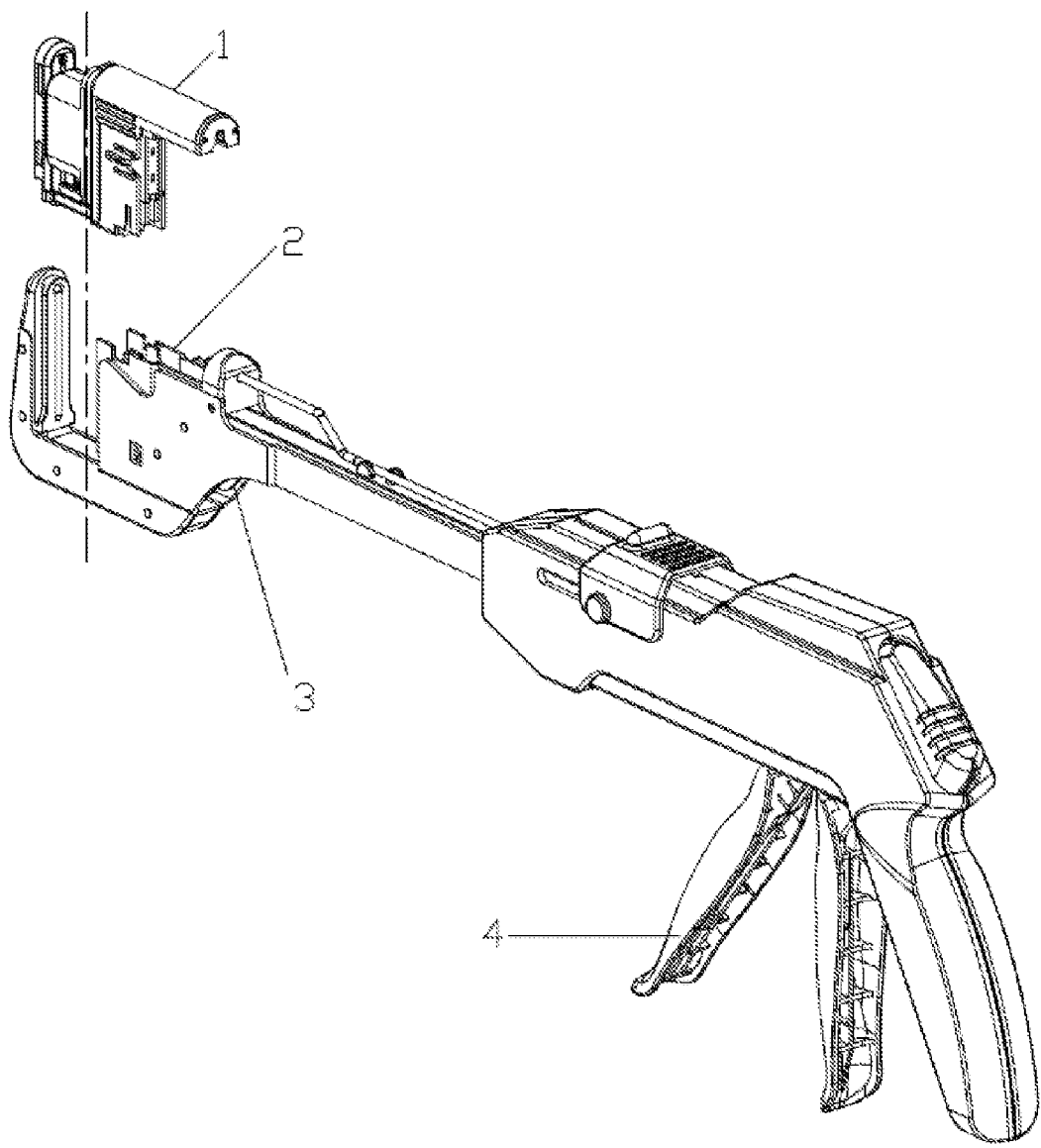
FIG. 17 is a structure and its use state schematic diagram of the cutting element of the present invention.

As shown in FIGS. 15 and 16, the E-shaped face 144 of the guiding element 16 is arranged at the open end 126 of the nail cartridge 14, the open nail cartridge has the disadvantages of existing shrinkage or extension deformation after machining; the guiding element 16 enables nail grooves at the two sides of the nail cartridge 14 to remain parallel vertically, which enables the nail cartridge 14 in an open state to be in a closed state; the guiding element 16 also enables the nail abutting plate 11 to be connected to the nail cartridge 14. The feed slot 123 of the nail cartridge 14 contains positioning bosses 127, 128, 129 for cutting tool, and the width between the positioning bosses is slightly larger than the thickness of the cutting tool 18, thereby preventing the deflection phenomenon of the cutting tool 18. The positioning bosses also enable to effectively control the deformation of the nail cartridge generated in machining.

The operating principle of the present invention is as follows:

The linear cutting element 1 is loaded into the linear cutting anastomat 2, and the linear cutting element 1 is in an initial installation status. After removing the assembly cover 12 from the linear cutting element 1, operating the linear cutting anastomat 2, the linear cutting element 1 is conducted to be in a closed operation status. The handle 4, driving board 3 of the linear cutting anastomat 2 push the bottom of the tool apron 19 of the linear cutting element 1, the end face of the tool apron 19 push the bottom of the push sheet 15, suturing nails 13 on the end face of the push sheet 15 conduct a movement of tissue suture in relative to a molding groove of a nail abutting plate 11, and the cutting tool 18 fixed on a tool apron 19 conduct a movement of tissue cutting in relative to the tool underlaying plate 10, so that the suture and cutting of the tissue are simultaneously accomplished in one operation. Conduct the reset device of the linear cutting anastomat 2, the tool apron 19, cutting tool 18 and other components of the linear cutting element 1 are reset to an initial status through the driving board 3 (see FIGS. 1 to 17).

What is claimed is:

1. A linear cutting element with an E-shaped guiding element comprising a tool underlying plate, a nail abutting seat, an assembly cover, a suturing nail, a nail cartridge, a push sheet, a guiding element, a guiding element pin, a cutting tool, a tool apron, a positioning needle, a positioning needle holder and a blank cap; the tool underlying plate and the nail abutting seat are fixedly connected by a front-end groove and a rear-end barb of the tool underlying plate;

the nail abutting seat is fixedly connected with the guiding element by the guiding element pin;

the guiding element is arranged at an open end of the nail cartridge, and the guiding element enables nail grooves at the two sides of the nail cartridge to remain parallel vertically, which enables the nail cartridge in an open state to be in a closed state;

the assembly cover is arranged between the nail abutting seat and the nail cartridge, and can be removed from the linear cutting element.

2. The linear cutting element with an E-shaped guiding element according to claim 1, characterized in that, the guiding element is in clearance fit with the nail cartridge, and both the guiding element and the nail cartridge can move vertically relative to each other.

3. The linear cutting element with an E-shaped guiding element according to claim 1, characterized in that, the cross profile of the guiding element is an E-shape.

4. The linear cutting element with an E-shaped guiding element according to claim 1, characterized in that, one end of the nail cartridge is open.

5. The linear cutting element with an E-shaped guiding element according to claim 1, characterized in that, the middle of the nail cartridge is provided with at least one positioning boss for a cutting tool.

6. The linear cutting element with an E-shaped guiding element according to claim 1, characterized in that, the tool apron is provided with at least two slots to receive the driving board of the linear cutting anastomat.

7. The linear cutting element with an E-shaped guiding element according to claim 1, characterized in that, the nail abutting seat shows an L-shape.

8. The linear cutting element with an E-shaped guiding element according to claim 1, characterized in that, one end of the assembly cover is an elastic finger.

9. The linear cutting element with an E-shaped guiding element according to claim 1, characterized in that, the linear cutting element is replaceably loaded into the linear cutting anastomat.

\* \* \* \* \*